United States Patent
Shin et al.

(10) Patent No.: US 12,383,894 B2
(45) Date of Patent: Aug. 12, 2025

(54) EXTRACTION APPARATUS, EXTRACTION METHOD, AND FLUIDIC CHIP FOR EXTRACTING TARGET MATERIAL

(71) Applicant: Korea University Research and Business Foundation, Seoul (KR)

(72) Inventors: Se-Hyun Shin, Seoul (KR); Ho-Yoon Lee, Seoul (KR); Won-Hwi Na, Seoul (KR); Chan-Hee Park, Buan-gun (KR)

(73) Assignee: Korea University Research and Business Foundation, Seoul (KR)

(*) Notice: Subject to any disclaimer, the term of this patent is extended or adjusted under 35 U.S.C. 154(b) by 896 days.

(21) Appl. No.: 17/430,422

(22) PCT Filed: Feb. 12, 2020

(86) PCT No.: PCT/KR2020/001989
§ 371 (c)(1),
(2) Date: Aug. 12, 2021

(87) PCT Pub. No.: WO2020/166980
PCT Pub. Date: Aug. 20, 2020

(65) Prior Publication Data
US 2022/0126284 A1    Apr. 28, 2022

(30) Foreign Application Priority Data
Feb. 14, 2019   (KR) .................. 10-2019-0017054

(51) Int. Cl.
*B01L 3/00* (2006.01)
*C12N 15/10* (2006.01)

(52) U.S. Cl.
CPC .......... *B01L 3/5023* (2013.01); *B01L 3/561* (2013.01); *C12N 15/1006* (2013.01); *C12N 15/1017* (2013.01); *B01L 2200/0668* (2013.01); *B01L 2300/042* (2013.01); *B01L 2300/043* (2013.01); *B01L 2300/0681* (2013.01); *B01L 2300/069* (2013.01); *B01L 2300/0832* (2013.01); *B01L 2300/0861* (2013.01); *B01L 2400/043* (2013.01); *B01L 2400/049* (2013.01); *B01L 2400/06* (2013.01)

(58) Field of Classification Search
CPC ........ B01L 3/5023; B01L 3/561; B01L 3/502; B01L 3/5027; C12N 15/1006; C12N 15/1017; C12N 15/1013
USPC ..................................................... 536/25.41
See application file for complete search history.

(56) References Cited

U.S. PATENT DOCUMENTS

2017/0029810 A1    2/2017 Hamada et al.

FOREIGN PATENT DOCUMENTS

| KR | 10-0601974 B1 | 7/2006 |
|---|---|---|
| KR | 10-1495631 B1 | 2/2015 |
| KR | 10-2016-0138578 A | 12/2016 |

OTHER PUBLICATIONS

Chen et al., Published Apr. 17, 2010, Biomedical Microdevices, vol. 12, pp. 705-719 (Year: 2010).*
Zhang et al., Published Feb. 15, 2011, Lab on a Chip, vol. 11, Issue 7, pp. 1271-1275 (Year: 2011).*
Lee, Hoyoon, et al., "Centrifugation-Free Extraction of Circulating Nucleic Acids using Immiscible Liquid under Vacuum Pressure," *Scientific reports*, 8, 1, 2018 (pp. 1-11).
International Search Report issued on Aug. 26, 2020 in counterpart International Patent Application No. PCT/KR2020/001989 (2 pages in English and 2 pages in Korean).
Lee, Hoyoon, et al. "Centrifugation-free extraction of circulating nucleic acids using immiscible liquid under vacuum pressure." Scientific reports 8.1 (2018): 5467., (11 pages).
Chinese Office Action issued on Feb. 28, 2024, in counterpart Chinese Patent Application No. 202080025737.2 (10 pages in Chinese).
Lee, Hoyoon, et al. "Centrifugation-free extraction of circulating nucleic acids using immiscible liquid under vacuum pressure." *Scientific reports* vol. 8. Issue 1 (2018): 5467. pp 1-11.
Chinese Office Action issued on Aug. 21, 2023, in corresponding Chinese Patent Application No. 202080025737.2 (9 pages in Chinese).

* cited by examiner

*Primary Examiner* — Renee Claytor
*Assistant Examiner* — Jaret J Crews
(74) *Attorney, Agent, or Firm* — NSIP Law

(57) ABSTRACT

The present invention relates to an extraction apparatus, extraction method, and fluidic chip for extracting a target material. In the extraction apparatus according to the present invention, in a state in which a target material is bound to a porous film in an extraction kit, when an elution solution and a magnetic solution sequentially pass, the elution solution remaining in the porous film is pushed out by the magnetic solution due to a difference in polarity, and collected in a collection chamber. In addition, even in the collection chamber, the elution solution and the magnetic solution are maintained in a stacked state due to different polarities, and in a state in which the magnetic solution in the collection chamber is physically separated from the elution solution by magnetism of a magnetism applicator, the elution solution in the collection chamber may be recovered. Accordingly, after the elution solution is collected in the collection chamber along with the magnetic solution, in a state in which the magnetic solution in the collection chamber is physically separated from the elution solution by magnetism, the elution solution may be recovered.

8 Claims, 16 Drawing Sheets

[FIG. 1]
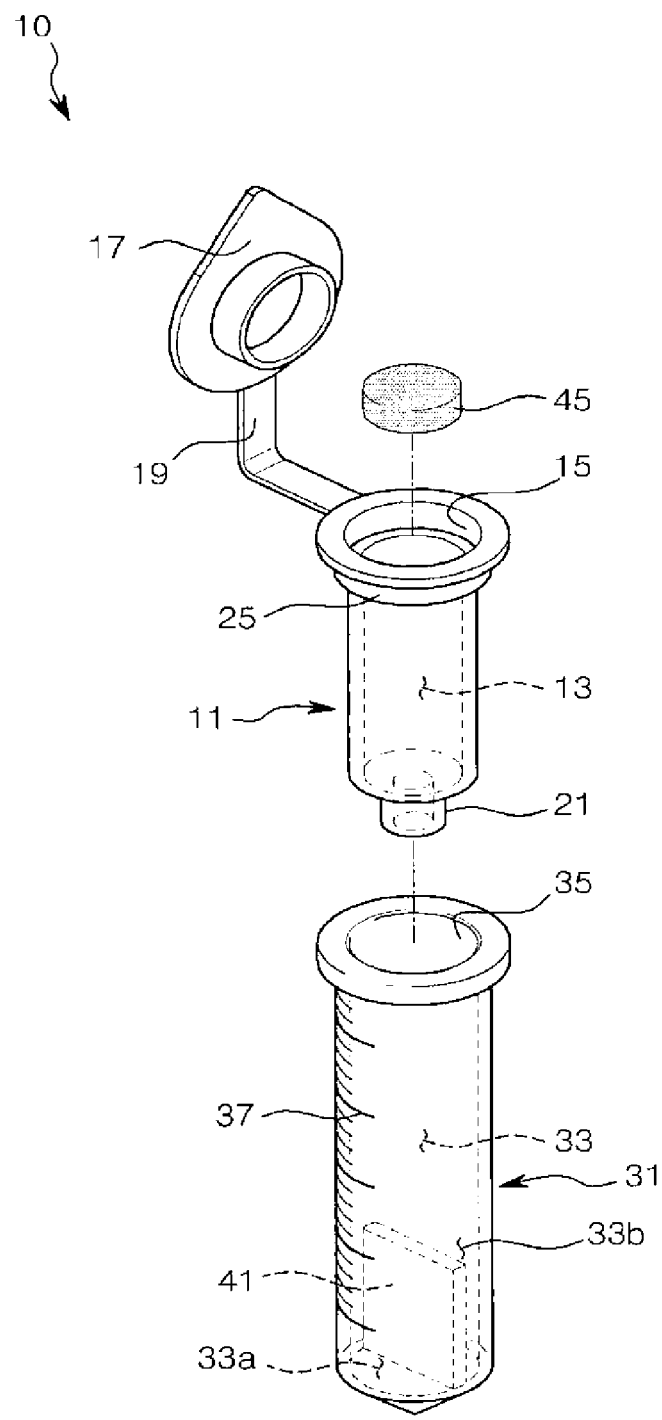

[FIG. 2]
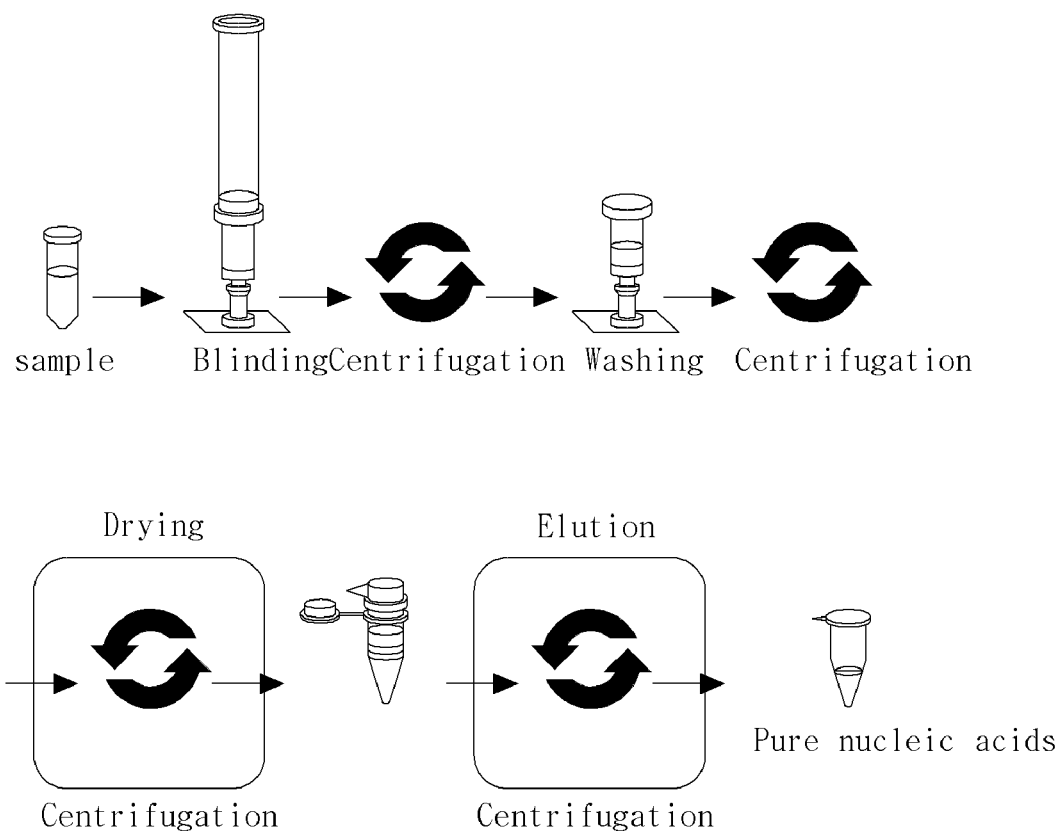

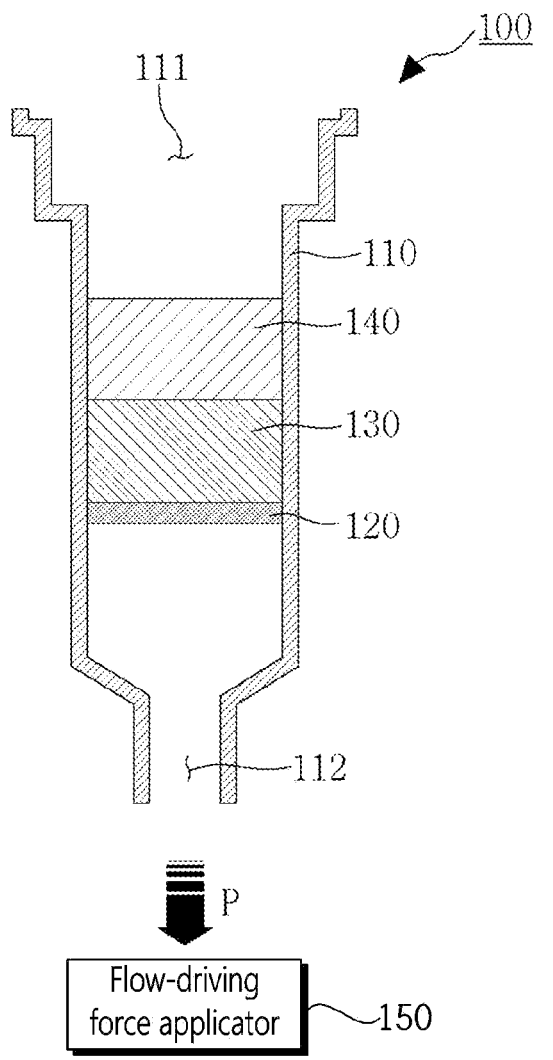
[FIG. 3]

[FIG. 4]
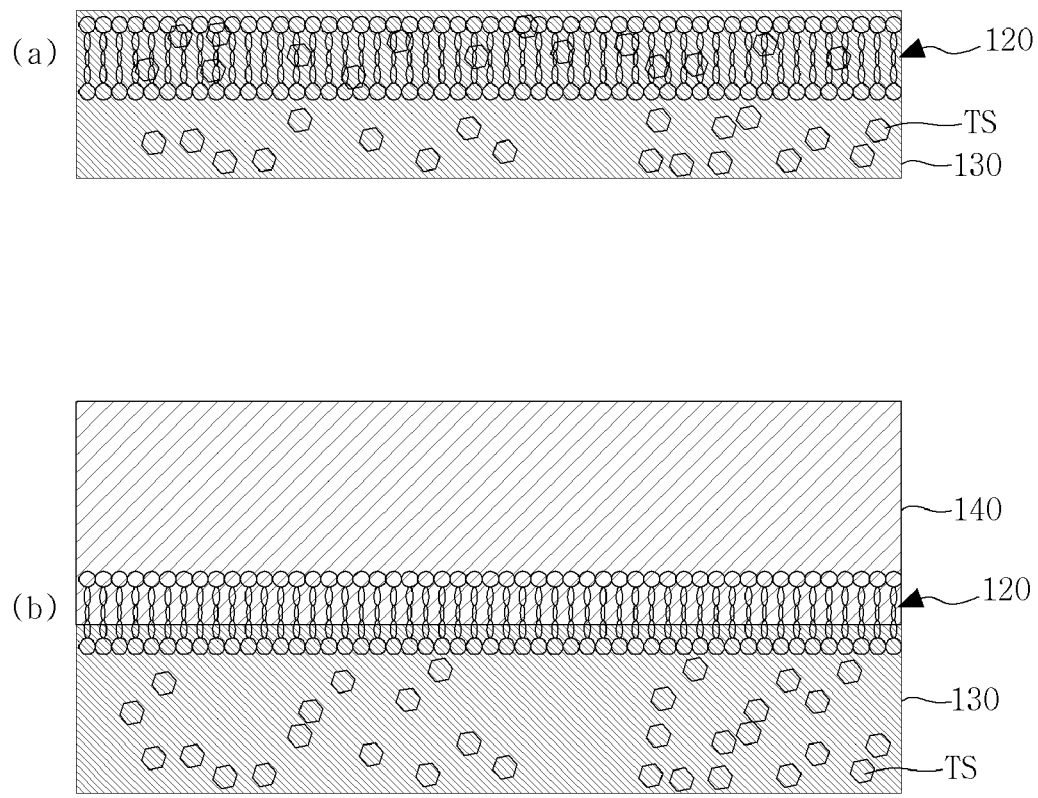

[FIG. 5]
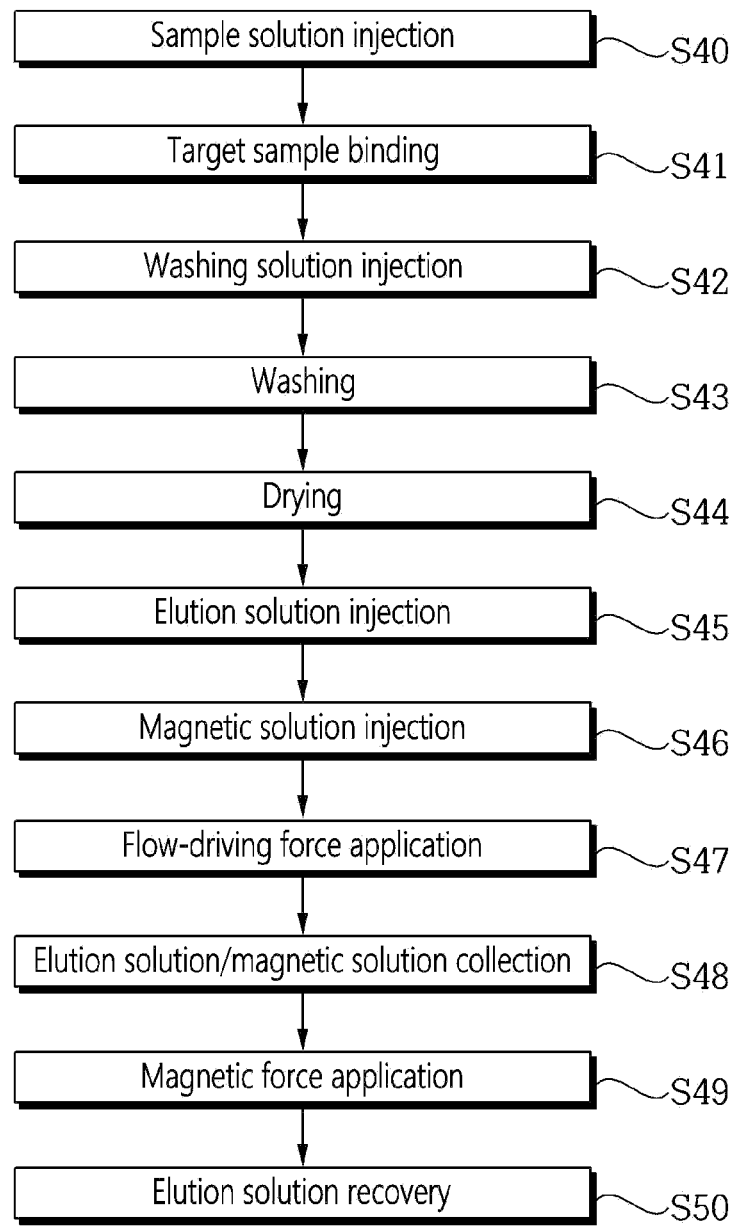

[FIG. 6]
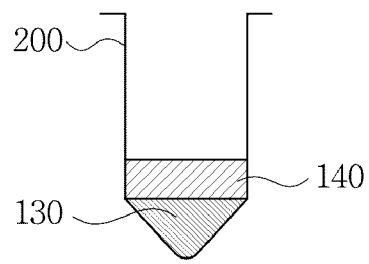
(a)
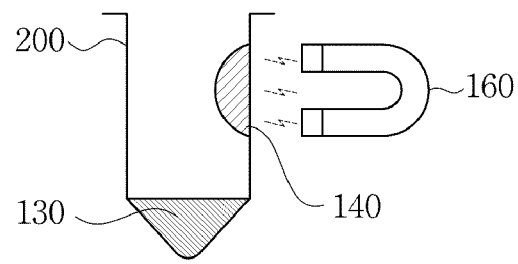
(b)
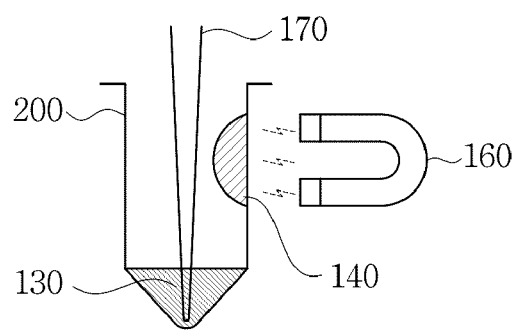
(c)
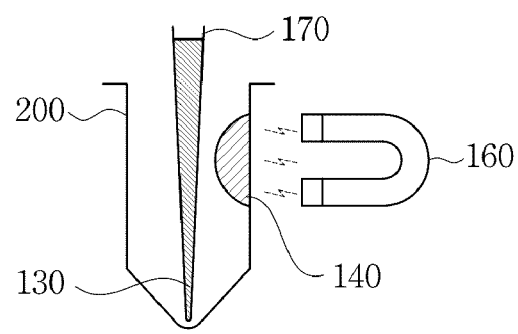
(d)

[FIG. 7]
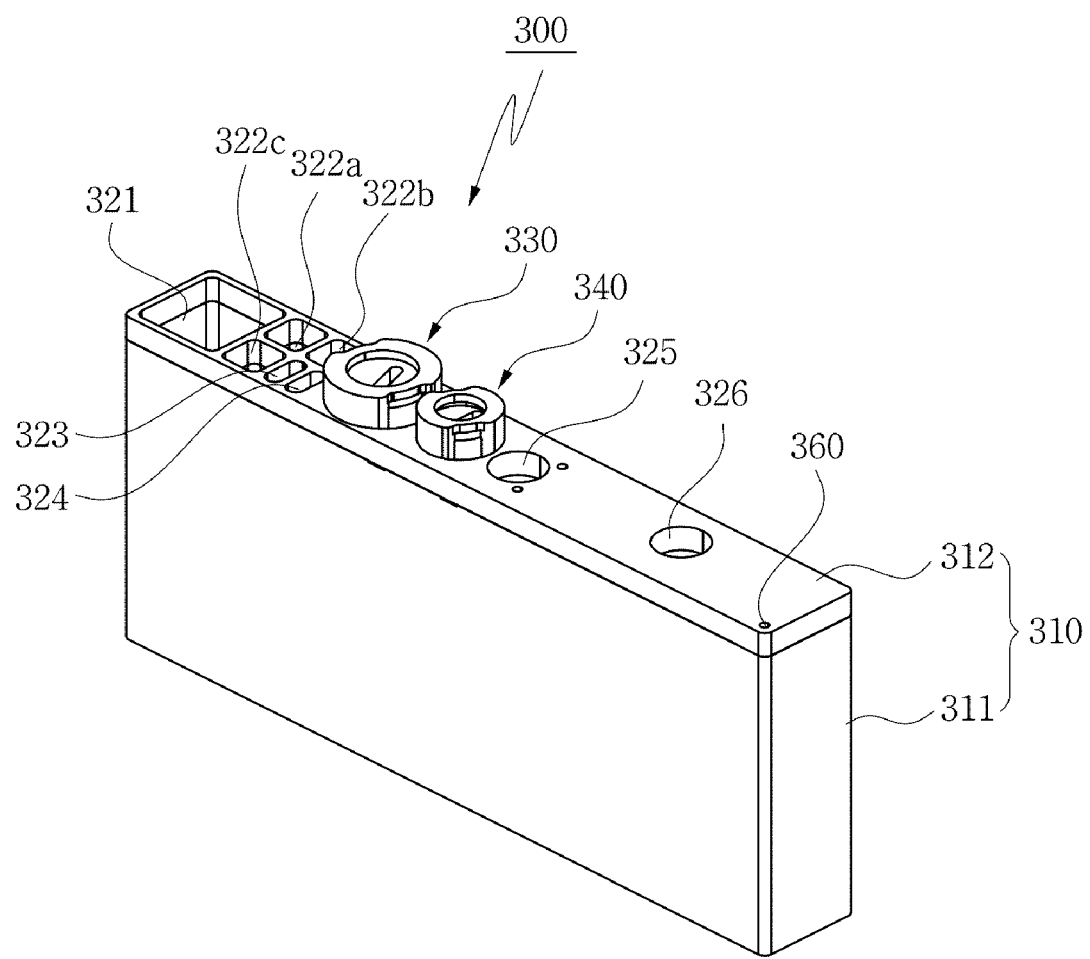

[FIG. 8]
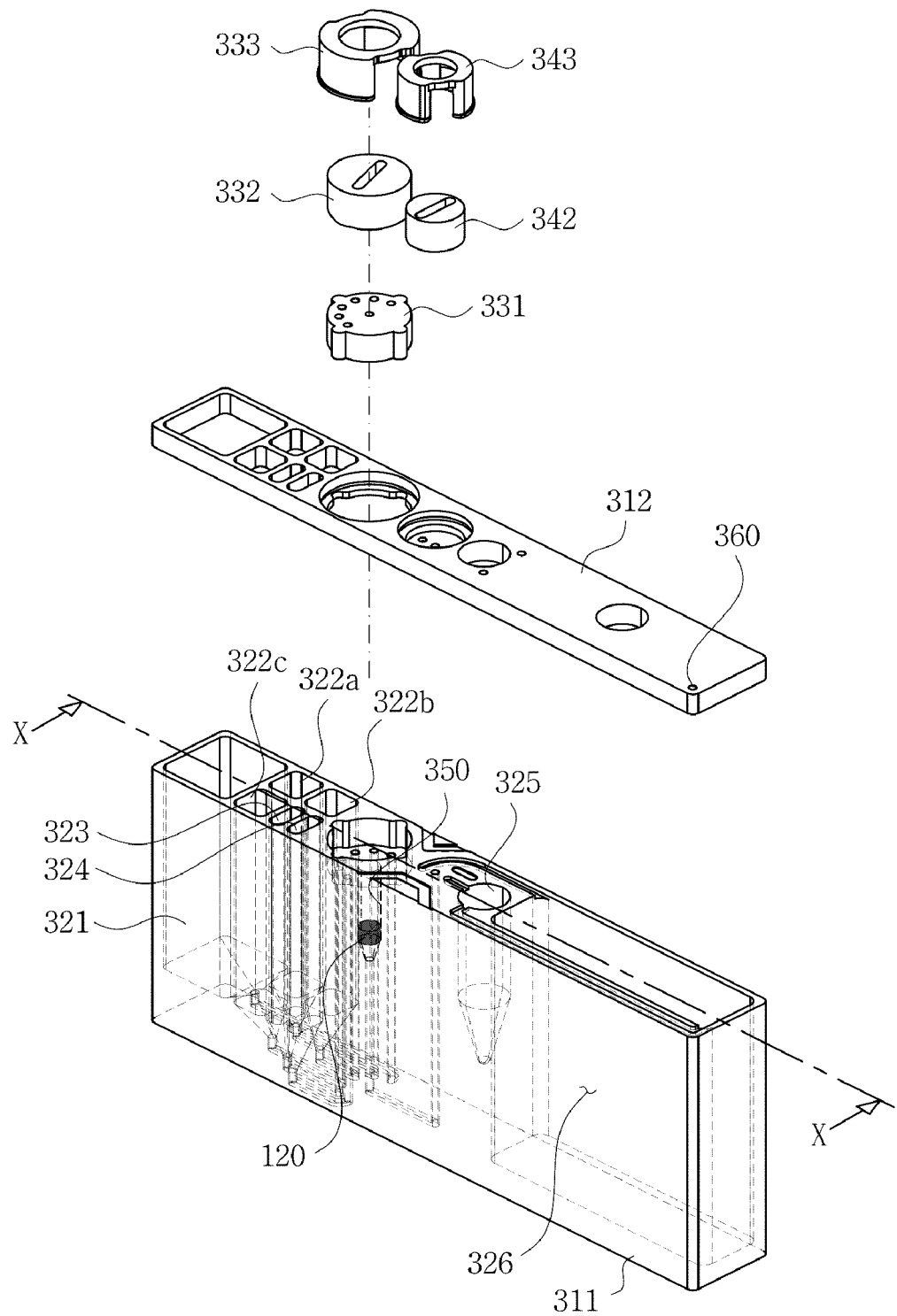

[FIG. 9]
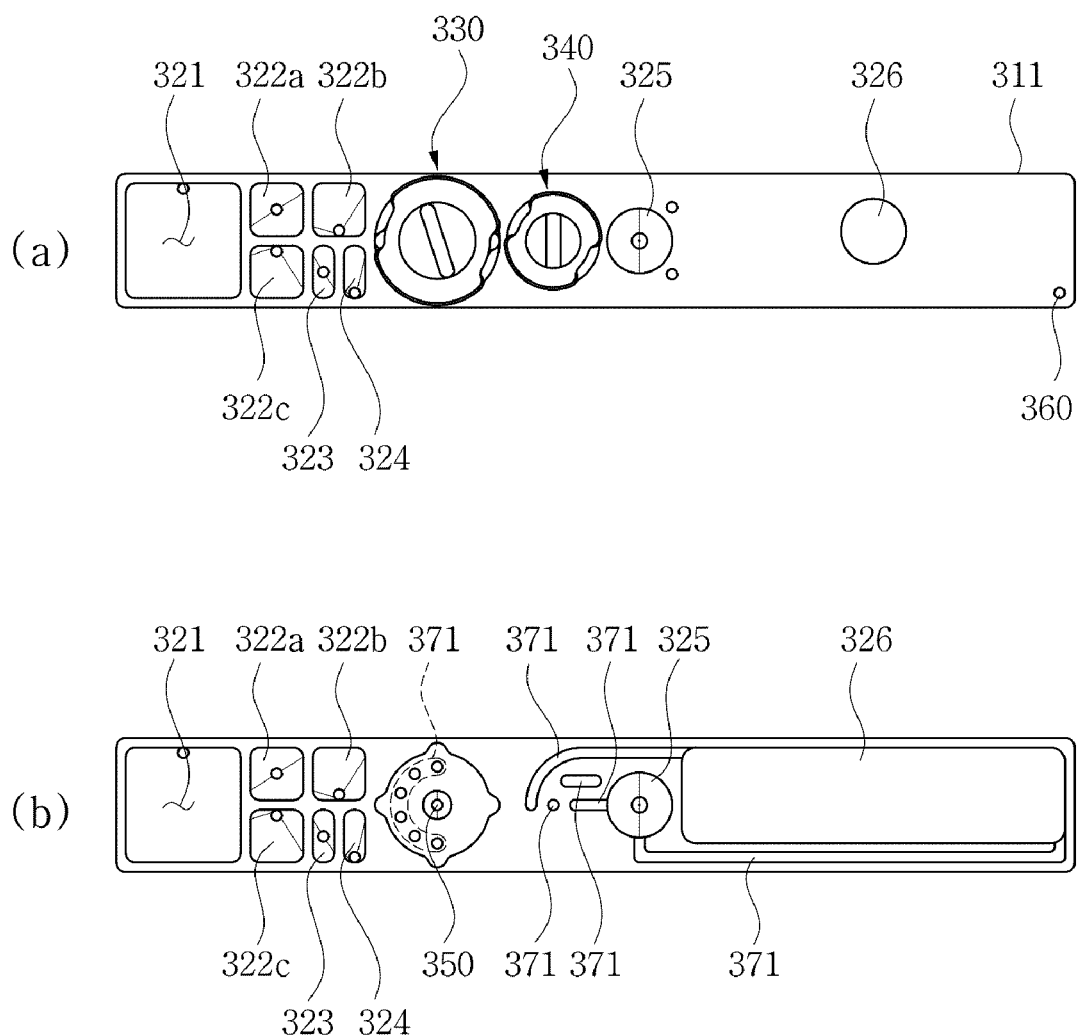

[FIG. 10]
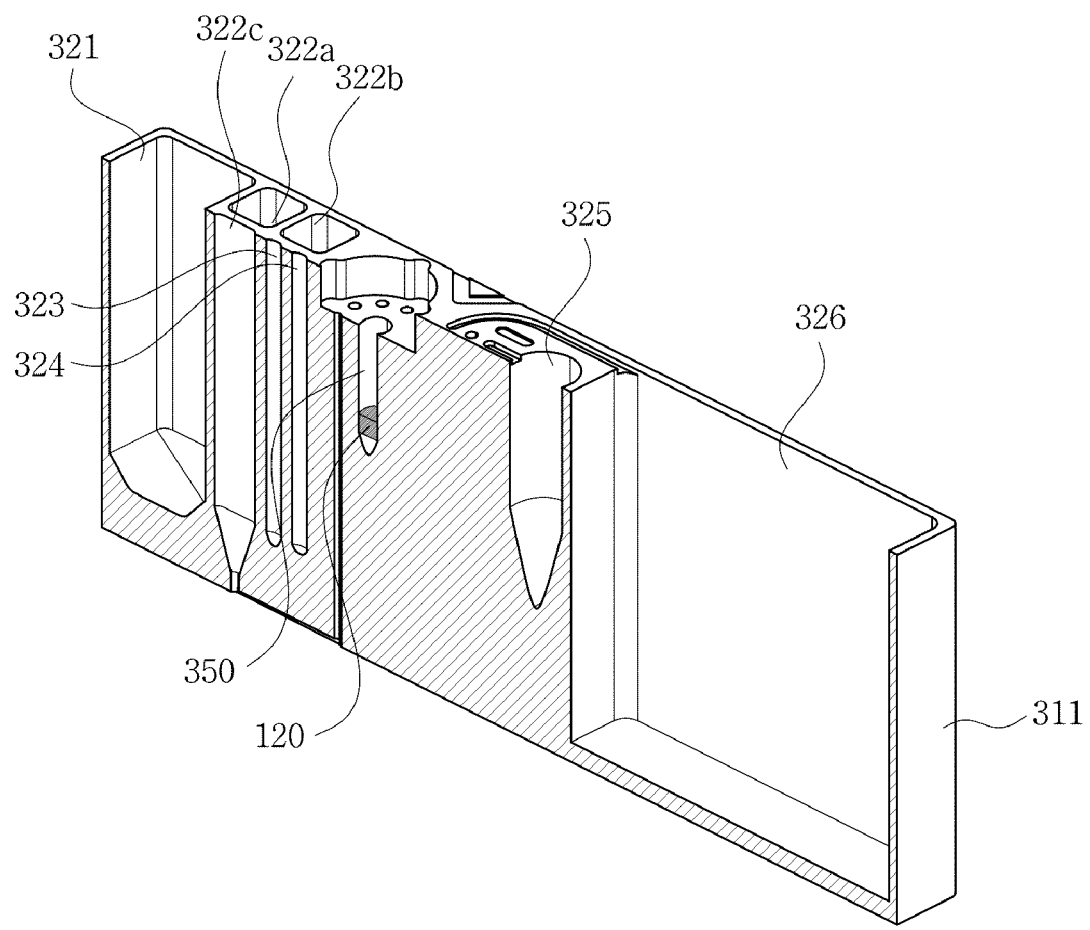

[FIG. 11]
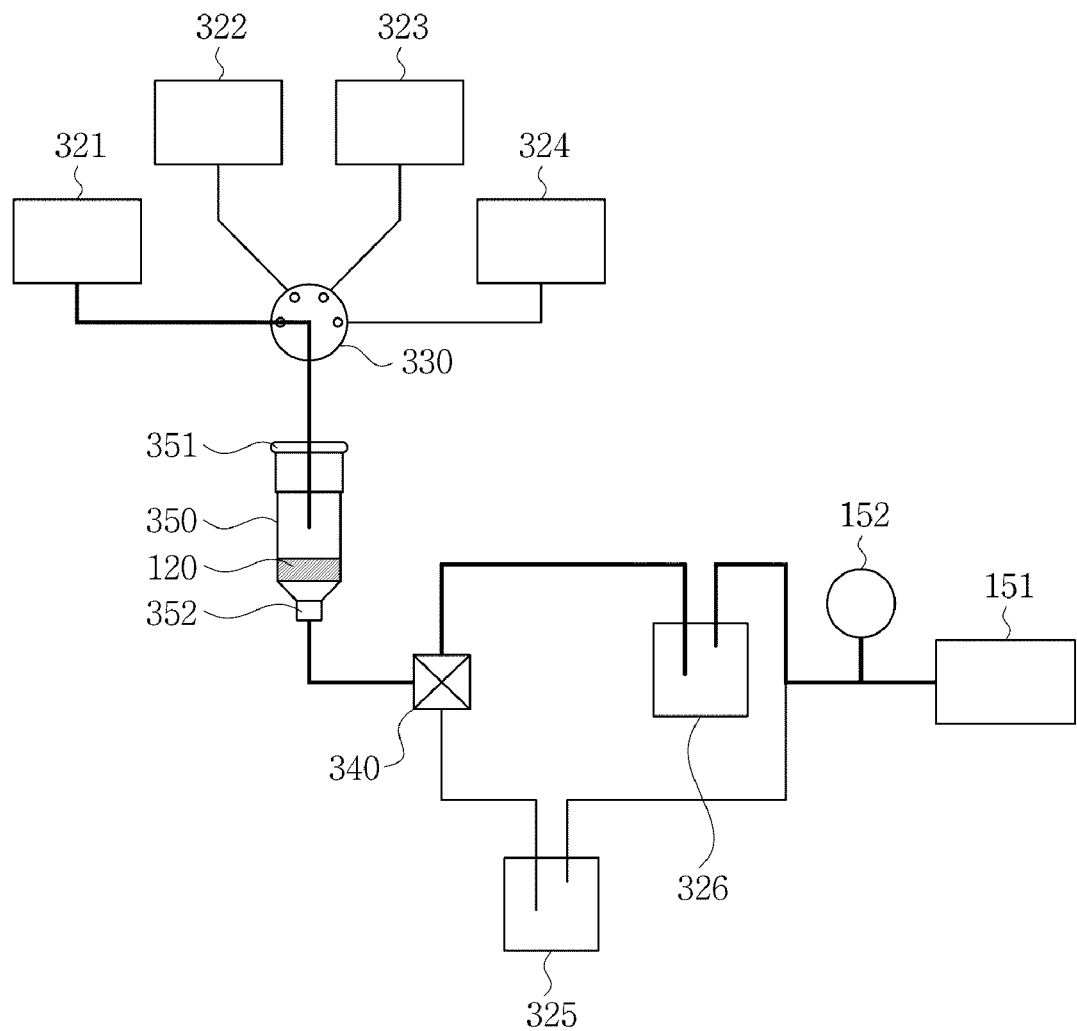

[FIG. 12]
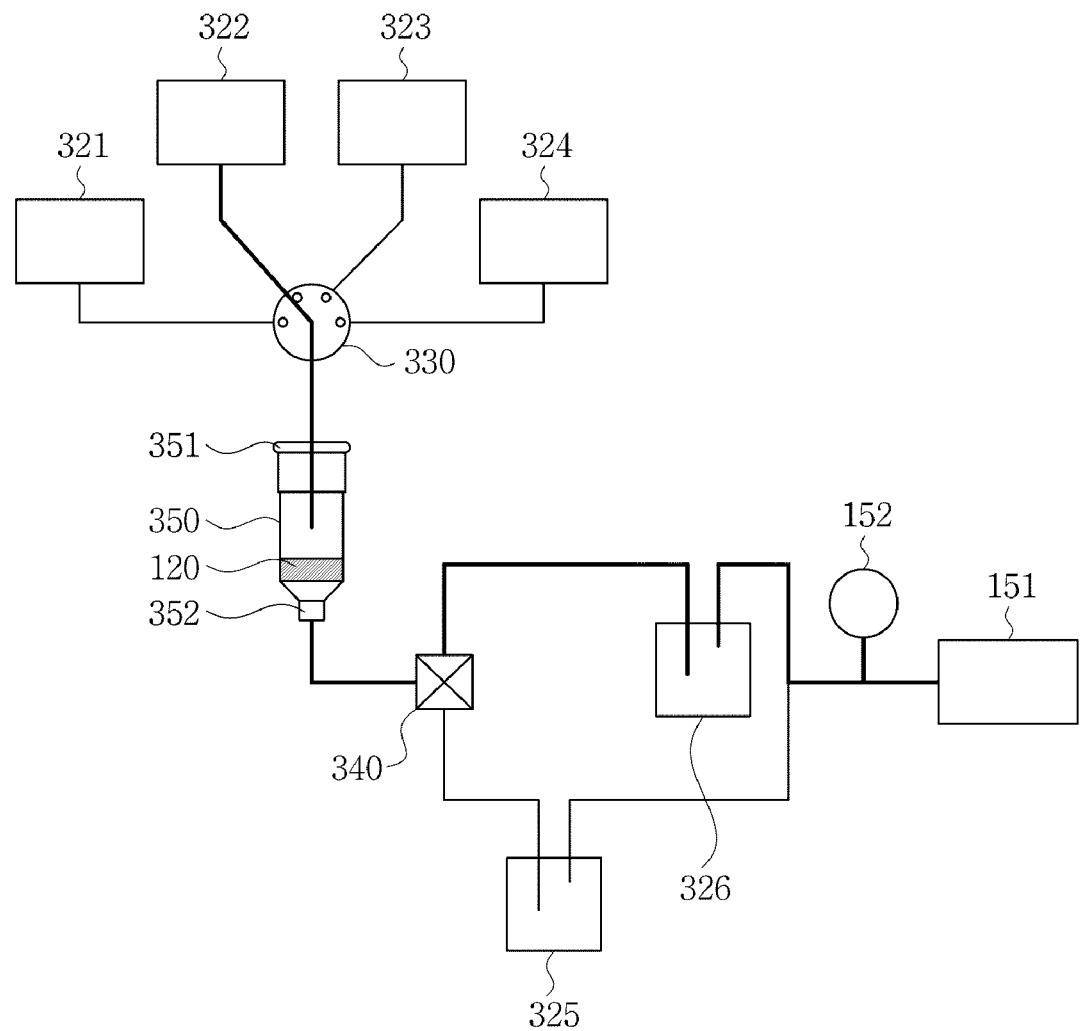

[FIG. 13]
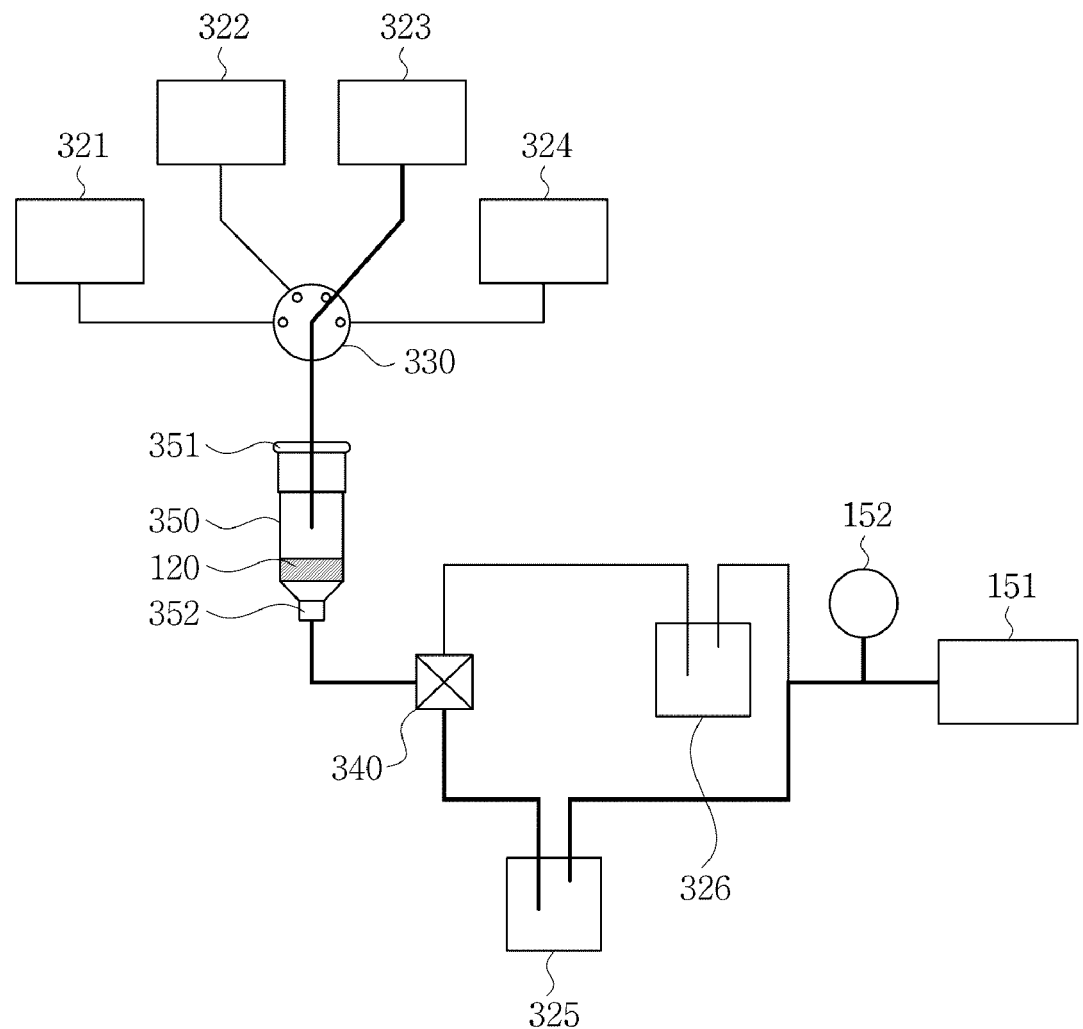

[FIG. 14]
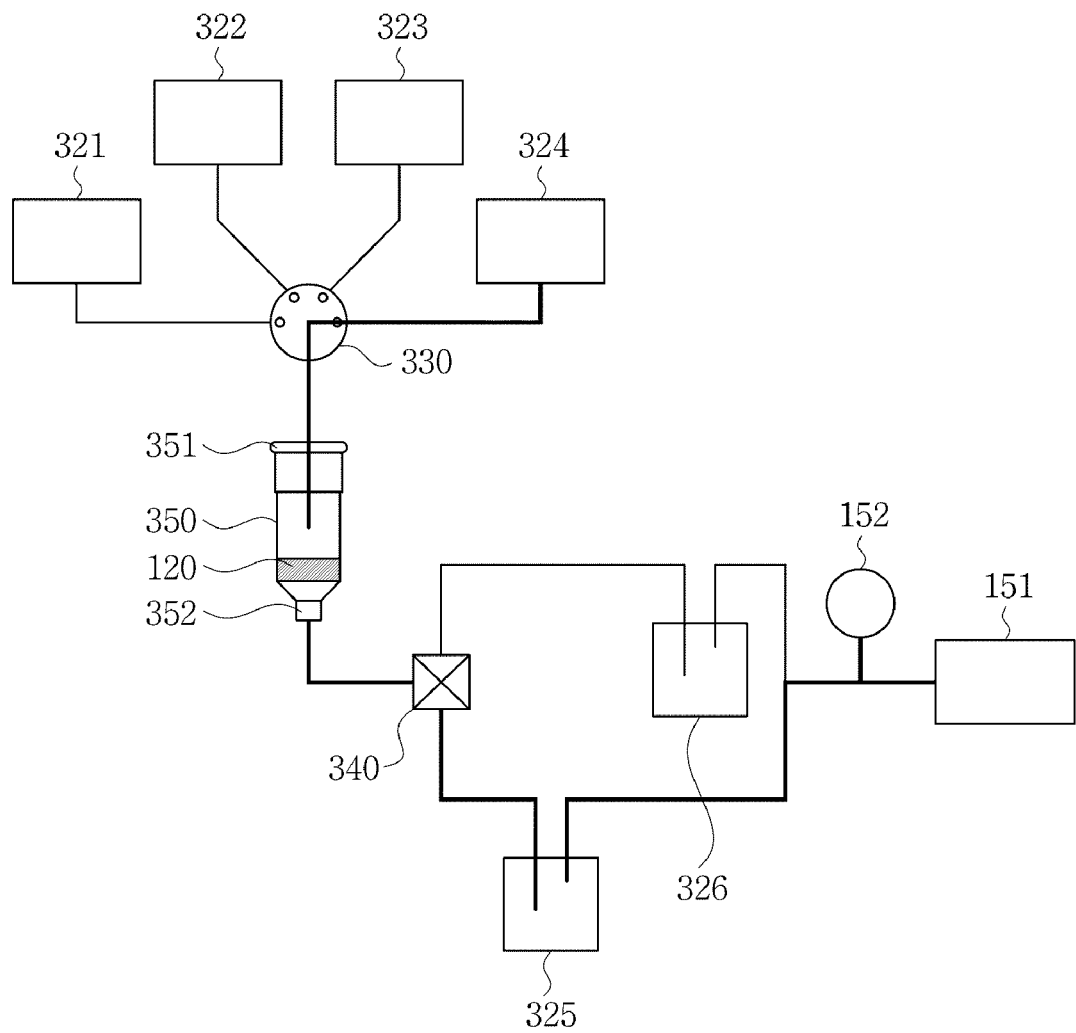

[FIG. 15]
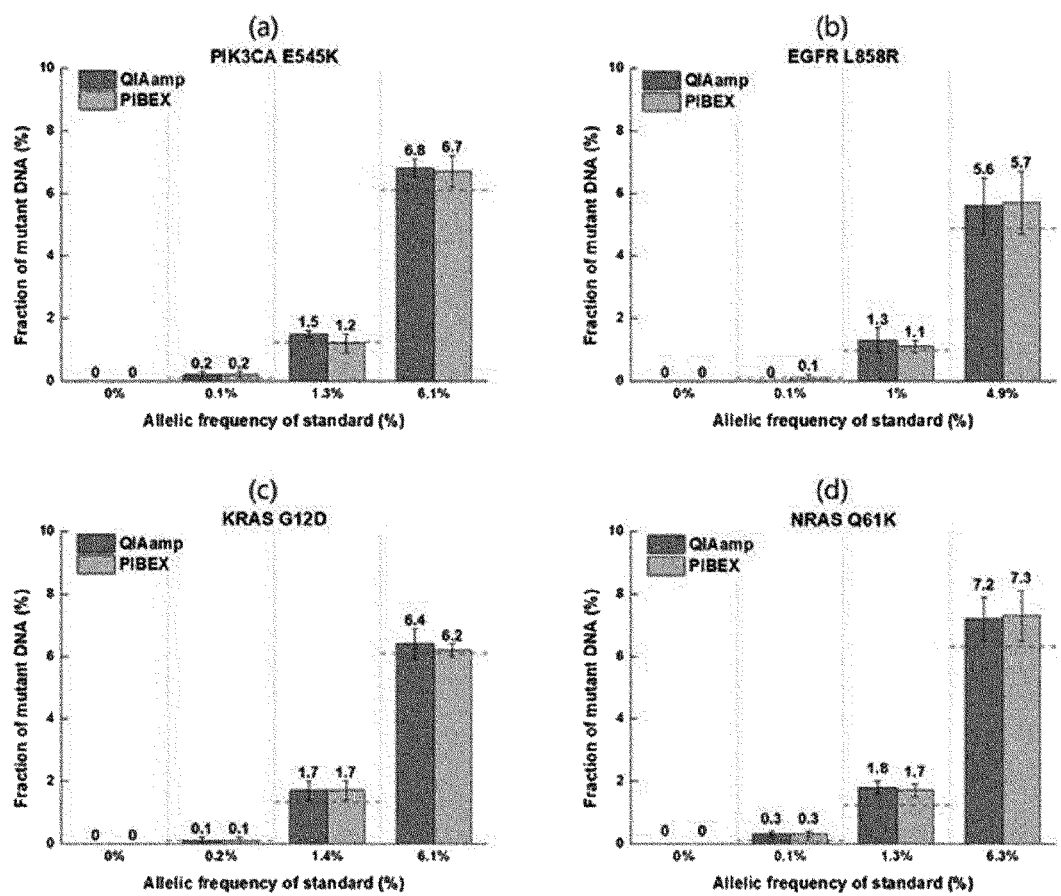

[FIG. 16]
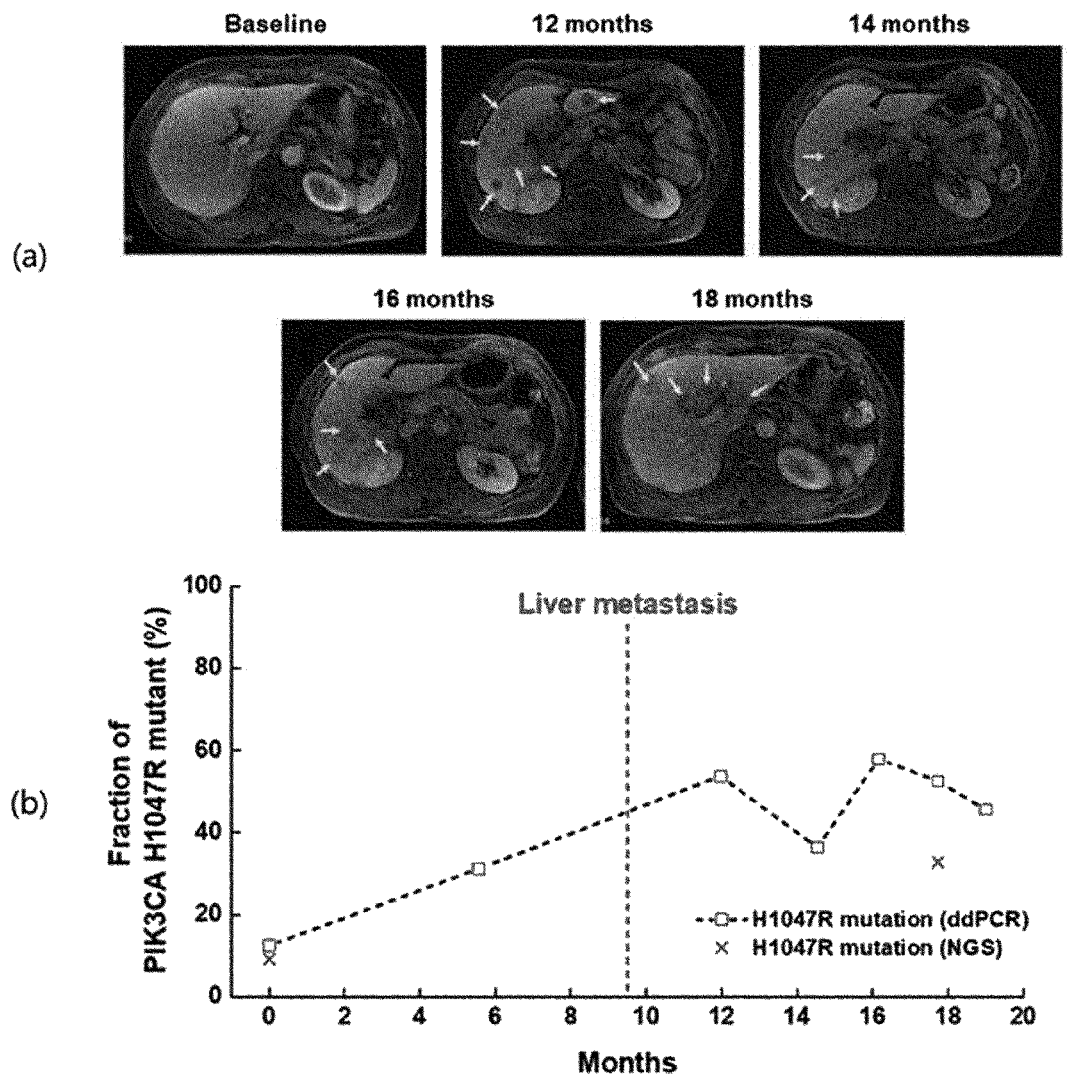

EXTRACTION APPARATUS, EXTRACTION METHOD, AND FLUIDIC CHIP FOR EXTRACTING TARGET MATERIAL

CROSS REFERENCE TO RELATED APPLICATIONS

This application is a U.S. National Stage Application of International Application No. PCT/KR2020/001989, filed on Feb. 12, 2020, which claims the benefit under 35 USC 119(a) and 365(b) of Korean Patent Application No. 10-2019-0017054, filed on Feb. 14, 2019, in the Korean Intellectual Property Office, the entire disclosure of which is incorporated herein by reference for all purposes.

FIELD

The present disclosure relates to an extraction device, an extraction method, and a fluidic chip for extracting a target substance. More particularly, the present disclosure relates to an extraction device, an extraction method, and a fluidic chip capable of extracting a target substance such as a nucleic acid without using a centrifugation scheme or without applying high-speed centrifugation.

RELATED ART

In a medical field, efficient diagnosis and treatment methods for realizing customized medicine are being actively developed. Extraction and purification of target substances such as nucleic acids are key processes in biotechnology, molecular biology, biochemistry, and diagnostic testing medicine.

In recent years, non-invasive liquid biopsy has been attracting attention as a practical alternative to conventional tissue biopsy as it has proven its high detection accuracy and qualification as an early detection marker. In this connection, demand for separation and purification technologies such as cfDNA (cell free DNA), exosomes, and CTC (Circulating Tumor Cell) from blood or other body fluids is increasing.

An example of a typical target substance pretreating method for rapid and accurate diagnosis may include a nucleic acid extraction process in a spin column scheme which is configured to sequentially flow samples and buffers for nucleic acid extraction to a column including a porous membrane made of silica. As a result, the spin column scheme is intended for binding nucleic acids to a porous membrane, washing the same, and concentrating the nucleic acids to a desired concentration and extracting the nucleic acids.

FIG. 1 is a diagram showing an example of a column disclosed in Korean Patent No. 10-1495631, and FIG. 2 is a diagram showing a process of extracting nucleic acids using a spin column scheme.

As described with reference to FIG. 2, when a sample including nucleic acid is put into the column and then subjected to a centrifugation process in a centrifugal separator, the nucleic acid in the sample is bound to the porous membrane. Then, a washing solution is injected into the column and the centrifugation process is performed again using a centrifugal separator, such that impurities remaining in the porous membrane are removed. In the connection, in the washing process, various washing solutions may be used or the process may be performed multiple times depending on the type of the nucleic acid or body fluid from which the nucleic acid is extracted, or a subsequent nucleic acid treating process.

When the washing process is completed, a drying process is performed so that the washing solution remaining on the porous membrane is completely removed. In this case, the drying process is generally executed via a centrifugation process using a centrifugal separator. When the drying process is completed, an elution solution or elution buffer is injected into the column, and then the centrifugation process is performed using a centrifugal separator, so that the nucleic acid bound to the porous membrane may be extracted together with the elution solution.

As described above, in the nucleic acid extraction using the spin column scheme, the centrifugation process is required in most of steps. Recently, a scheme using a negative pressure has been proposed in the binding process or the washing process. However, in this approach, 12,000 G or greater must be applied to the column during the drying process or elution process, especially the elution process. Thus, it is difficult to replace the centrifugation process with the negative pressure based scheme.

In this centrifugation process, when extracting nucleic acids, the column must be placed in the centrifugal separator and then taken out therefrom in each process. This makes it difficult to separate nucleic acids using a series of processes on a single chip.

Further, it is difficult to apply the spin column scheme to on-site diagnosis where the centrifugal separator cannot be placed. There is a risk of cross-contamination during a process of transferring the sample extracted from the field to the place where the centrifugal separator is provided.

Further, since the user has to manually perform a series of processes, the repetition accuracy of the nucleic acid extraction amount or purity is affected according to the user's skill level.

DISCLOSURE

Technical Purpose

Accordingly, the present disclosure has been devised to solve the above problems. Thus, a purpose of the present disclosure is to provide an extraction device, an extraction method, and a fluidic chip capable of extracting a target substance such as nucleic acid without using a centrifugation scheme or without applying high-speed centrifugation.

Technical Solution

One aspect of the present disclosure provides an extraction device for extracting a target substance, the device comprising: an extraction kit, a porous membrane installed inside the extraction kit, wherein the target substance is bound to the porous membrane; an elution solution for eluting the target substance from the porous membrane while passing through the porous membrane in the extraction kit; a magnetic solution having magnetism and having a different polarity from a polarity of the elution solution such that magnetic solution is not mixed with the elution solution; a collection chamber for collecting therein the elution solution and the magnetic service sequentially passing through the porous membrane in a stacked and separated state; and a magnetic force applicator for applying a magnetic force to the collection chamber, wherein when the magnetic solution passes through the porous membrane, the elution solution remaining in the porous membrane is repelled from the porous membrane due to the different polarity of the magnetic solution from the polarity of the elution solution, wherein while the magnetic solution in the collection chamber is physically separated from the elution solution using a magnetic force from the magnetic force applicator, the elution solution in the collection chamber is recovered.

In one implementation of the device, the magnetic force applicator applies a magnetic force to an outer side face of the collection chamber so that the magnetic solution flows toward and is agglomerated on a corresponding inner side face of the collection chamber such that the elution solution below the magnetic solution is exposed upwardly.

In one implementation of the device, the elution solution is a polar solution, and the magnetic solution is a non-polar solution.

In one implementation of the device, when the target substance is a nucleic acid, the elution solution includes polar distilled water or an elution buffer for nucleic acid extraction, and the magnetic solution includes non-polar mineral oil or silicone oil containing magnetic particles dispersed therein.

In one implementation of the device, the device further comprises a flow-driving force applicator for applying a flow-driving force to the extraction kit such that the elution solution and the magnetic solution pass through the porous membrane.

In one implementation of the device, the extraction kit includes: an inlet through which the elution solution and the magnetic solution are injected into the extraction kit; and an outlet through which the elution solution which passed through the porous membrane is discharged, wherein the flow-driving force applicator includes a pressure pump for applying a positive pressure into the extraction kit through the inlet or for applying a negative pressure into the extraction kit through the outlet.

Another aspect of the present disclosure provides an extraction method for extracting a target substance using an extraction device, the method comprising: providing an extraction kit having a porous membrane installed therein; binding the target substance to the porous membrane; eluting the target substance from the membrane while passing an elution solution through the porous membrane; repelling the elution solution remaining in the porous membrane from the porous membrane while passing a magnetic solution through the porous membrane, wherein the magnetic solution has magnetism and has a polarity different from a polarity of the elution solution; collecting the elution solution and the magnetic solution sequentially passing through the porous membrane into a collection chamber, in which the elution solution and the magnetic solution are stacked into the collection chamber in a separate manner due to the different polarities thereof; and recovering the elution solution from the collection chamber; wherein recovering the elution solution includes: applying a magnetic force from an outside of the collection chamber to the collection chamber such that the magnetic solution is physically separated from the elution solution; and recovering the separated elution solution from the collection chamber.

In one implementation of the method, recovering the elution solution includes: applying the magnetic force to an outer side face of the collection chamber so that the magnetic solution flows toward and is agglomerated on a corresponding inner side face of the collection chamber so that the elution solution is exposed upwardly; and recovering the upwardly-exposed elution solution from the collection chamber.

In one implementation of the method, the elution solution is a polar solution, and the magnetic solution is a non-polar solution.

In one implementation of the method, when the target substance is a nucleic acid, the elution solution includes polar distilled water or an elution buffer for nucleic acid extraction, and the magnetic solution includes non-polar mineral oil or silicone oil containing magnetic particles dispersed therein.

In one implementation of the method, the extraction kit has: an inlet through which the elution solution and the magnetic solution are injected into the extraction kit; and an outlet through which the elution solution passing through the porous membrane is discharged, wherein a flow-driving force for driving flow of the elution solution and the magnetic solution is applied to the extraction kit, wherein the flow-driving force includes a positive pressure applied into the extraction kit through the inlet or a negative pressure into the extraction kit through the outlet.

Still another aspect of the present disclosure provides a fluidic chip for extracting a target substance, the fluidic chip comprising: a chip body; a sample chamber formed inside the chip body to store therein a sample solution containing the target substance; an elution chamber formed inside the chip body to store therein an elution solution for elution of the target substance; a magnetic chamber formed inside the chip body to store therein a magnetic solution, wherein the magnetic solution has a magnetism and has a polarity different from a polarity of the elution solution such that the magnetic solution is not mixed with the elution solution; an extraction chamber formed inside the chip body; a porous membrane installed inside the extraction chamber, wherein the target substance is bound to the porous membrane; a chamber selection valve installed on the chip body to selectively connect one of the sample chamber, the elution chamber, and the magnetic chamber to the inlet of the extraction chamber; and a collection chamber formed inside the chip body and connected to the outlet of the extraction chamber; wherein the chamber selection valve sequentially connects the extraction chamber to the elution chamber and the magnetic chamber, and then a flow-driving force from an outside is applied such that the elution solution and the magnetic solution respectively in the elution chamber and the magnetic chamber sequentially pass through the inlet and then the porous membrane, wherein when the magnetic solution passes through the porous membrane, the magnetic solution expels the elution solution remaining in the porous membrane out of the membrane, and then the elution solution and magnetic solution are collected into the collection chamber through the outlet, wherein the elution solution and the magnetic solution are stacked in the collection chamber in a separate manner according to the different polarities thereof, wherein a magnetic force is applied to the collection chamber from an outside thereof so that the magnetic solution is physically separated from the elution solution in the collection chamber, and then the elution solution is recovered from the collection chamber.

In one implementation of the fluidic chip, the magnetic force applied to the collection chamber from the outside is applied to an outer side face of the collection chamber so that the magnetic solution flows toward and is agglomerated on a corresponding inner side face of the collection chamber while the elution solution below the magnetic solution is exposed upwardly.

In one implementation of the fluidic chip, the chip body includes: a lower body having the sample chamber, the elution chamber, the magnetic chamber, the extraction chamber, and the collection chamber defined therein; and an upper cover coupled to a top face of the lower body, wherein flow channels for respectively connecting the sample chamber, the elution chamber, and the magnetic chamber with the inlet of the extraction chamber are defined in the lower body, wherein a distal end of each of the flow channels and the inlet of the extraction chamber are open toward a top of the chip body, wherein the chamber selection valve is coupled to the lower body via the upper cover and selectively connects one of the distal ends of the flow channels respectively connected to the sample chamber, the elution chamber, and the magnetic chamber to the inlet of the extraction chamber.

In one implementation of the fluidic chip, the fluidic chip further comprises: at least one washing chamber defined in the lower body to accommodate therein a washing solution; a waste solution chamber defined in the lower body to store therein the sample solution and the washing solution that have passed through the extraction chamber; and a discharge selection valve coupled to the lower body via the upper cover to selectively connect the outlet of the extraction chamber to one of the collection chamber and the waste solution chamber, wherein after the target substance in the sample solution binds to the porous membrane, the washing solution in the washing chamber passes through the extraction chamber to wash the porous membrane.

In one implementation of the fluidic chip, the chip body further has a negative pressure inlet connected to the collection chamber and the waste solution chamber, wherein a negative pressure from an outside is introduced thereto through the negative pressure inlet, wherein the negative pressure inlet applies the negative pressure to the outlet of the collection chamber through the collection chamber or waste solution chamber based on selection of the discharge selection valve.

In one implementation of the fluidic chip, the elution solution is a polar solution, and the magnetic solution is a non-polar solution.

In one implementation of the fluidic chip, when the target substance is a nucleic acid, the elution solution includes polar distilled water or an elution buffer for nucleic acid extraction, and the magnetic solution includes non-polar mineral oil or silicone containing magnetic particles dispersed therein.

In one implementation of the fluidic chip, when the target substance is a nucleic acid, the porous membrane includes one of a silica membrane, an ion exchange resin, a silica mesh, a packing tube in which silica beads are packed, and a membrane having a surface having a functional group attached thereto capable of specific-binding to the target substance, or wherein when the target substance includes one of a cell including CTC (Circulating Tumor Cell), an extracellular vesicle including exosome, and a protein, the porous membrane includes one of an ion exchange resin, and a membrane having a surface having a functional group attached thereto capable of specific-binding to the target substance.

In one implementation of the fluidic chip, the target substance includes one of a nucleic acid including DNA and RNA, a cell including CTC (Circulating Tumor Cell), an extracellular vesicle including exosome, and a protein.

Technical Effect

According to the present disclosure, the extraction device, the extraction method, and the fluidic chip capable of extracting the target substance such as the nucleic acid without using a centrifugation scheme or without applying high-speed centrifugation may be realized.

BRIEF DESCRIPTION OF DRAWINGS

FIG. 1 is a view showing an example of a column disclosed in Korean Patent No. 10-1495631.

FIG. 2 is a diagram showing a process of extracting nucleic acids using a spin column scheme.

FIG. 3 is a diagram showing a configuration of an extraction device for extracting a target substance according to the present disclosure.

FIG. 4 is a diagram to illustrate a principle of operation of an extraction device for extracting a target substance according to the present disclosure.

FIG. 5 is a diagram to illustrate an extraction method for extracting the target substance according to the present disclosure.

FIG. 6 is a diagram for illustrating a process of recovering an elution solution from the elution solution and a magnetic solution collected in a collection chamber in an extraction device for extracting the target substance according to the present disclosure.

FIG. 7 is a perspective view of a fluidic chip for extracting a target substance according to the present disclosure.

FIG. 8 is an exploded perspective view of the fluidic chip shown in FIG. 7.

(a) in FIG. 9 is a plan view of the fluidic chip shown in FIG. 7.

(b) of FIG. 9 is a plan view of a lower body of the fluidic chip shown in FIG. 8.

FIG. 10 is a cross-sectional view taken along a X-X line of FIG. 8.

FIG. 11 to FIG. 14 are diagrams to illustrate an extraction process of a target substance using a fluidic chip according to the present disclosure, FIG. 15 is a diagram to illustrate experimental results using a fluidic chip according to the present disclosure.

FIG. 16 is a diagram showing experimental results of monitoring a mutant gene via blood analysis of a patient in actual clinical practice using a fluidic chip according to the present disclosure.

BEST MODE

Hereinafter, embodiments according to the present disclosure will be described in detail with reference to the accompanying drawings.

FIG. 3 is a diagram showing a configuration of an extraction device 100 for extracting a target substance according to the present disclosure. Referring to FIG. 3, the extraction device 100 according to the present disclosure includes an extraction kit 110, a porous membrane 120, an elution solution 130, and a magnetic solution 140. Further, the extraction device 100 according to the present disclosure may include a collection chamber 200 (see FIG. 6) and a flow-driving force applicator 150.

The extraction kit 110 has a cylindrical shape in which an inlet 111 and an outlet 112 are formed. According to the present disclosure, it is exemplified that the kit has a cylindrical shape. Moreover, the elution solution 130 and the magnetic solution 140 flow into the kit through the inlet 111. The elution solution 130 and the magnetic solution 140 that have passed through the porous membrane 120 are discharged through the outlet 112. According to the present disclosure, an example in which an inner diameter of the outlet 112 is narrower that that of the inlet 111 is set forth.

The porous membrane 120 is installed inside the extraction kit 110. A target substance TS (see FIG. 4) is bound to the porous membrane 120. In this connection, a binding process of the target substance TS may include previously known steps, such as a binding step, a washing step, and a drying step. The target substance TS may be bound to the porous membrane 120 using an extraction method or a fluidic chip 300 according to the present disclosure, which will be described later, and a detailed description thereof will be described later.

In this connection, the target substance TS to which the extraction device 100 according to the present disclosure is applied may include one of nucleic acid including DNA and RNA, cells including CTC (Circulating Tumor Cell), extracellular vesicles including exosomes, and proteins.

Further, when the target substance TS is a nucleic acid, the porous membrane 120 may include one of a silica membrane, an ion exchange resin, a silica mesh, a packing tube in which silica beads are closed packed, or a membrane having a functional group disposed on a surface thereof capable of specific binding to the target substance TS. Further, when the target substance TS includes one of the cell including CTC (Circulating Tumor Cell), the extracellular vesicles including exosomes, and the protein, the porous membrane 120 may include one of an ion exchange resin and membrane having a functional group disposed on a surface thereof capable of specific binding to the target substance TS. The porous membrane 120 may have various types of membrane structures in which the target substance TS is attached or specifically bound to the porous membrane 120.

The elution solution 130 is stacked on the porous membrane 120 in the extraction kit 110. Moreover, when the elution solution 130 passes through the porous membrane 120, the target substance TS bound to the porous membrane 120 is dissolved in the elution solution 130 or dispersed into the elution solution 130, such that the target substance TS together with the elution solution 130 escapes from the porous membrane 120.

The magnetic solution 140 has a different polarity from that of the elution solution 130, and thus is kept immiscible with the elution solution 130 when being injected into the extraction kit 110. Moreover, the magnetic solution 140 may have magnetism. For example, magnetic particles are dispersed in a magnetic solution having a polarity different from that of the elution solution 130, so that an entirety of the solution has magnetism.

In this connection, the magnetic solution 140 is stacked on the elution solution 130 in the extraction kit 110 as shown in FIG. 3. That is, the porous membrane 120, the elution solution 130, and the magnetic solution 140 are maintained in a stacked form. Thus, the elution solution 130 passes through the porous membrane 120 and then the magnetic solution 140 passes through the porous membrane 120.

According to the present disclosure, for example, the elution solution 130 is a polar solution, such as distilled water, and the magnetic solution 140 is a non-polar solution, such as oil. In one example, when the target substance TS is a nucleic acid, polar distilled water or an elution buffer for nucleic acid extraction may be applied as the elution solution 130. In this connection, the elution buffer for nucleic acid extraction is a commercial buffer solution applied to extract the nucleic acids. In one example, a pH 8.0 mixed solution of 10 mM Tris-Cl, 0.1 M EDTA, 20 μg/ml pancreatic RNase A, and 0.5% SDS may be applied as the elution buffer for nucleic acid extraction. In this connection, the magnetic solution 140 may include a non-polar mineral oil or silicone oil in which magnetic particles are dispersed.

According to the above configuration, when a flow-driving force to allow the elution solution 130 and the magnetic solution 140 to pass through the porous membrane 120 is applied to the extraction kit 110 using a flow-driving force applicator 150, the elution solution 130 first passes through the porous membrane 120 and then the elution solution 130 together with the target substance TS in the porous membrane 120 flows to the opposite side of the porous membrane 120, as shown in (a) of FIG. 4.

In this regard, conventionally, while the elution solution 130 passes through the porous membrane 120, a centrifugation scheme (12,000 G) was applied to separate most of the target substance TS from the porous membrane 120. However, in the extraction device 100 according to the present disclosure, after the elution solution 130 has passed through the porous membrane 120, the magnetic solution 140 passes through the porous membrane 120. Thus, the elution solution 130 remaining in the porous membrane 120 is pushed out, so that the elution solution 130 and the target substance TS are completely detachable from the porous membrane 120 as shown in (b) of FIG. 4. Accordingly, the present scheme may extract the target substance TS using the elution solution 130 without using the centrifugal separator or even at a pressure lower than 12,000 G when the centrifugal force is used.

According to the present disclosure, the flow-driving force applied using the flow-driving force applicator 150 may include a pressure such as a positive pressure or a negative pressure, a centrifugal force, gravity, or an inertial force. For example, the flow-driving force applicator 150 may include a pressure pump that applies the positive pressure to an inside of the extraction kit 110 through the inlet 111 of the extraction kit 110 or applies the negative pressure to the inside of the extraction kit 110 through the outlet 112. In this connection, a compressor, a syringe pump, a peristaltic pump, etc. may be applied as the pressure pump.

Further, regarding the centrifugal force, the present scheme may easily separate the target substance TS even at a smaller rotational speed, that is, at a pressure lower than 12,000 G, compared to that in the prior art using the centrifugal force.

The gravity may be used as the flow-driving force. A flow resistance of the porous membrane 120 against the elution solution 103 is smaller. Thus, the elution solution 103 may pass through the porous membrane 120 under the gravity. Even when the residual the elution solution 130 that cannot pass through the porous membrane 120 remains in the porous membrane 120, the remaining the elution solution 130 is pushed out form the membrane using the magnetic solution 140 that may invade into the porous membrane 120 only under the gravity. Thus, the extraction of the target substance TS using the elution solution 130 may be realized.

Further, the inertial force may be used as the flow-driving force. In this case, while the elution solution 130 and the magnetic solution 140 are stacked on a top face of the porous membrane 120, the inertial force may be generated by repeating rapid movement in gravity direction and stop of the kit, thereby extracting the target substance TS using the elution solution 130.

In one example, the elution solution 130 and the magnetic solution 140 which sequentially passed through the porous membrane 120 in the extraction kit 110 are collected in the collection chamber 200 connected to the outlet 112 of the extraction kit 110. As shown in FIG. 6, the elution solution 130 and the magnetic solution 140 are collected in a stacked and separated state according to mutually different polarities. Moreover, a process of recovering the elution solution 130 from the collection chamber using the magnetism of the magnetic solution 140 may be carried out. Detailed descriptions thereof will be made with reference to the extraction method for extracting the target substance TS according to the present disclosure with reference to FIG. 5 and FIG. 6.

First, as shown in FIG. 3, the extraction kit 110 with the porous membrane 120 installed therein is prepared. Moreover, the target substance TS is bound to the porous membrane 120 of the extraction kit 110. When this process is described in more detail with reference to FIG. 5, a sample solution containing the target substance TS is injected into the extraction kit 110 with the porous membrane 120 installed therein S40.

Then, when the flow-driving force for the flow of the sample solution is applied to the extraction kit 110, the sample solution passes through the porous membrane 120, such that the target substance TS in the sample solution is bound to the porous membrane 120 S41. Then, the washing solution is injected into the extraction kit 110 S42, and the flow-driving force is applied thereto, such that the washing solution passes through the porous membrane 120 and washes the inside of the porous membrane 120 S43. Moreover, a drying process is performed after the completion of the washing step. In this way, the binding of the target substance TS to the inside of the porous membrane 120 is completed.

Then, the elution solution 130 and the magnetic solution 140 are injected into extraction kit 110 S45 and S46. In FIG. 5, the injection of the magnetic solution 140 after the injection of the elution solution 130 is shown by way of example. However, when the elution solution 130 is distilled water with polarity, and the magnetic solution 140 is a non-polar oil, the elution solution 130 and the magnetic solution 140 are sequentially stacked on the porous membrane 120 as shown in FIG. 3, regardless of the injection order thereof.

After the injection of the elution solution 130 and the magnetic solution 140 is completed, the flow-driving force is applied to the extraction kit 110 S47. Thus, as described above, the elution solution 130 first passes through the porous membrane 120, and then the remaining target substance TS together with the elution solution 130 are pushed out of the porous membrane 120 using the magnetic solution 140, so that the remaining target substance TS may be completely extracted together with the elution solution 130. In this connection, a scheme for applying the flow-driving force to the extraction kit 110 is the same as described above, and thus a detailed description thereof is omitted.

Moreover, when a portion or an entirety of the magnetic solution 140 has passed through the porous membrane 120, the elution solution 130 and the magnetic solution 140 are collected in the collection chamber 200 as shown in (a) of FIG. 6 S48. In this connection, in the collection chamber 200, the elution solution 130 and the magnetic solution 140 are collected in a stacked and separated state according to mutually different polarities, as shown in (a) of FIG. 6.

In the state shown in (a) of FIG. 6, the lower elution solution 130 may be recovered using a pipette tip 170. During the recovery process, a portion of the magnetic solution 140 may be collected together therewith to reduce a purity. When the recovery is stopped before the magnetic solution 140 is recovered to improve the purity, a recovery efficiency of the target substance TS is reduced.

Accordingly, according to the present disclosure, as shown in (b) of FIG. 6, a magnetic force applicator 160 applies S49 a magnetic force from the outside of the collection chamber 200 to physically separate the magnetic solution 140 from the elution solution 130. In this state, the elution solution 130 may be recovered S50. According to the present disclosure, it is exemplified that the magnetic force applicator 160 is embodied as a permanent magnet. Alternatively, the magnetic force applicator 160 may be embodied as an electromagnet.

Moreover, in (b) of FIG. 6, the magnetic force applicator 160 applies a magnetic force to a side face of the collection chamber 200 so that the magnetic solution 140 aggregates on the side face of the collection chamber 200. As a result, while as shown in (c) of FIG. 6, the pipette tip 170 is directly immersed in the elution solution 130 without passing through the magnetic solution 140, the elution solution 130 may be recovered as shown in (d) of FIG. 6. Moreover, after the elution solution 130 has been recovered, the target substance TS is extracted from the elution solution 130.

In the above-described embodiment, the elution solution 130 and the magnetic solution 140 are injected into extraction kit 110, and then the flow-driving force is applied in a state where the elution solution 130 and the magnetic solution 140 are stacked on the porous membrane 120 in a separated state. However, the present disclosure is not limited thereto. The elution solution 130 and the magnetic solution 140 may not be stacked in the extraction kit 110. That is, the elution solution 130 first flows into the extraction kit 110, and passes through the porous membrane 120, and then, the elution solution 130 is first collected into the collection chamber 200. Then, the magnetic solution 140 passes through the porous membrane 120 flows into the extraction kit 110, and passes through the porous membrane 120, and then, the is collected into the collection chamber 200.

Fluidic Chip

Hereinafter, a fluidic chip 300 for extracting the target substance according to the present disclosure will be described in detail with reference to FIG. 7 to FIG. 14. The fluidic chip 300 according to the present disclosure refers to an example in which the above-described extraction device is implemented in a form of a chip, and the extraction kit 110 is embodied as an extraction chamber 350 in the fluidic chip 300. Further, an example in which the flow-driving force applicator 150 in the above embodiment is embodied as a negative pressure pump 151 and a pressure gauge 152 shown in FIG. 11 to FIG. 14 will be described below. The reference number of the porous membrane has the same 120.

When being described with reference to FIG. 7 to FIG. 10, the fluidic chip 300 according to the present disclosure includes a chip body 310, a sample chamber 321, an elution chamber 323, a magnetic chamber 324, an extraction chamber 350, a porous membrane 120, a chamber selection valve 330 and a collection chamber 325.

For example, the chip body 310 is made of a transparent or translucent plastic material. According to the present disclosure, as shown in FIG. 8, the chip body 310 includes a lower body 311 and an upper cover 312 by way of example. The sample chamber 321, the elution chamber 323, the magnetic chamber 324, the extraction chamber 350 and the collection chamber 325 are disposed in the lower body 311, and flow channels 371 for connecting these chambers are formed.

The upper cover 312 is coupled to a top face of the lower body 311. The upper cover 312 has a structure to block or cover all or some of the chambers as described above. A plug for opening and closing each chamber is coupled thereto.

The chamber selection valve 330 and a discharge selection valve 340 to be described later are coupled to the lower body 311 via the upper cover 312.

The sample chamber 321 is formed inside the lower body 311 of the chip body 310, and a sample solution containing the target substance is stored therein. Moreover, the elution chamber 323 and the magnetic chamber 324 are formed inside the lower body 311 of the chip body 310 and store therein the elution solution and the magnetic solution, respectively. In this connection, the elution solution and the magnetic solution may be the same as those with reference to the above-described extraction device 100, and detailed descriptions thereof are omitted.

The extraction chamber 350 is formed inside the lower chamber of the chip body 310, and corresponds to the extraction kit 110 of the above-mentioned extraction device 100. That is, in the extraction chamber 350, as shown in FIG. 7 and FIG. 10, the porous membrane 120 to which the target substance is bound is installed. Moreover, the collection chamber 325 is formed inside the lower body 311 of the chip body 310, and is connected to an outlet 352 (not shown) of the extraction chamber 350.

In one example, the chamber selection valve 330 is installed on the chip body 310 to selectively connect one of the sample chamber 321, the elution chamber 323 and the magnetic chamber 324 to the inlet 351 of the extraction chamber 350. According to the present disclosure, the chamber selection valve 330 is coupled to the lower body 311 via the upper cover 312, as shown in FIG. 8, by way of example.

Referring to FIG. 8 and (b) in FIG. 9, the lower body 311 has the flow channels 371 for connecting the sample chamber 321, the elution chamber 323 and the magnetic chamber 324 with the inlet 351 of the extraction chamber 350, respectively. In this connection, a distal end of the flow channel 371 is open toward a top face of the lower body 311 as shown in (b) of FIG. 9. Similarly, the inlet 351 of the extraction chamber 350 is open toward a top of the lower body 311. In this connection, the chamber selection valve 330 is coupled to the top face of the lower body 311 via the upper cover 312 to selectively connect one of distal ends of the flow channels 371 respectively connected to the sample chamber 321, the elution chamber 323 and the magnetic chamber 324 to the inlet 351 of the extraction chamber 350.

According to the present disclosure, as shown in FIG. 8, the chamber selection valve 330 includes a gasket 311 made of silicone, a chamber switching valve 332, and a first fixing jig 333 for fixing the gasket and the chamber switching valve. In this connection, the gasket 311 may have communication holes communicating with distal ends of the flow channels 371 and the inlet 351 of the extraction chamber 350. According to a rotation of the chamber switching valve 332, the inlet 351 of the extraction chamber 350 and the inlet 371 of each of the flow channels 371 may communicate with the communication holes, respectively.

In one example, the fluidic chip 300 according to the present disclosure may include at least one washing chamber 322a, 322b, and 322c, a waste solution chamber 326 and the discharge selection valve 340. The washing chambers 322a, 322b, and 322c are formed in the lower body 311 and accommodate therein a washing solution. According to the present disclosure, three washing chambers 322a, 322b, and 322c are arranged by way of example. However, the disclosure is not limited thereto. Washing solutions with different concentrations of ethanol are accommodated in the washing chamber 322a, 322b, and 322c, respectively. For example, the three washing chambers 322a, 322b, and 322c contain the washing solutions in a decreasing ethanol concentration order to sequentially wash the porous membrane 120 in the decreasing ethanol concentration order.

The waste solution chamber 326 is formed in the lower body 3111. Waste solutions such as the sample solution and the washing solution which have passed through the extraction chamber 350 may be stored therein. In this connection, the discharge selection valve 340 is coupled to the lower body 311 via the upper cover 312 to selectively connect the outlet 352 of the extraction chamber 350 to either the collection chamber 325 or the waste solution chamber 326. As shown in FIG. 8, the discharge selection valve 340 is composed of a discharge switching valve 342 and a second fixing jig 343 by way of example.

Further, a negative pressure inlet 360 connected to the collection chamber 325 and the waste solution chamber 326 is formed in the chip body 310. A negative pressure pump 151 is connected to the negative pressure inlet to apply a negative pressure for the fluid flow. That is, the negative pressure inlet 360 delivers the negative pressure for the flow of fluid to the outlet 352 of the collection chamber 325 through the collection chamber 325 or the waste solution chamber 326 according to a selection of the discharge selection valve 340. A detailed description thereof will be made later.

A process of extracting the target substance using the fluidic chip 300 according to the present disclosure having the above configuration will be described in detail with reference to FIG. 11 to FIG. 14.

First, as shown in FIG. 11, a binding step is performed in which in a state where the chamber selection valve 330 connects the extraction chamber 350 to the sample chamber 321, the sample solution accommodated in the sample chamber 321 is injected into the extraction chamber 350.

In the binding step, the discharge selection valve 340 is switched to connect the negative pressure pump 151 to the outlet 352 of the extraction chamber 350 through the waste solution chamber 326 as shown in FIG. 11. Accordingly, the sample solution in the sample chamber 321 is bound to an inside of the extraction chamber 350 via the chamber selection valve 330 under the negative pressure applied to the outlet 352 of the extraction chamber 350. In this connection, a line marked in a bold shape in FIG. 11 to FIG. 14 shows a connection line selected by each of the discharge selection valve 340 and the chamber selection valve 330.

Then, as shown in FIG. 12, while the chamber selection valve 330 connects the extraction chamber 350 to each of the washing chambers 322a, 322b, and 322c, the washing solution contained in each of the washing chambers 322a, 322b, and 322c is injected into the extraction chamber 350. Thus, a washing step is performed.

In the washing step, the discharge selection valve 340 is switched so that the negative pressure pump 151 is connected to the outlet 352 of the extraction chamber 350 through the waste solution chamber 326 as shown in FIG. 12. As a result, the washing solution in each of the washing chambers 322a, 322b, and 322c is injected into the extraction chamber 350 via the chamber selection valve 330 under the negative pressure applied to the outlet 352 of the extraction chamber 350. Then, the washing solution passes through the porous membrane 120. Thus, the washing process may be achieved. The washing solution which passed through the porous membrane 120 is discharged into the waste solution chamber 326 through the outlet 352 and the discharge selection valve 340.

FIG. 11 to FIG. 14 shows an example in which one of the washing chambers 322a, 322b, and 322c is applied. However, three washing solutions respectively from the three washing chambers 322a, 322b, and 322c may sequentially flow to wash the porous membrane 120.

Moreover, after performing the washing step as described above, the drying step may proceed. After completion of the drying step, the chamber selection valve 330 is switched so that the extraction chamber 350 and the elution chamber 323 are connected to each other. Thus, the elution solution in the elution chamber 323 flows into the extraction chamber 350.

In this connection, as shown in FIG. 13, the discharge selection valve 340 is switched so that the negative pressure pump 151 is connected to the outlet 352 side of the extraction chamber 350 via the collection chamber 325. As a result, the elution solution in the elution chamber 323 is injected into the extraction chamber 350 via the chamber selection valve 330 under the negative pressure applied to the outlet 352 of the extraction chamber 350 and then passes through the porous membrane 120, and then is collected into the collection chamber 325.

Then, the chamber selection valve 330 is switched so that the extraction chamber 350 and the magnetic chamber 324 are connected to each other as shown in FIG. 14. Thus, the magnetic solution in the magnetic chamber 324 is injected into the extraction chamber 350 and passes through the porous membrane 120 to push the remaining elution solution out of the membrane. Then, the magnetic solution together with the elution solution are collected in the collection chamber 325.

In this connection, as shown in FIG. 14, the discharge selection valve 340 is switched so that the negative pressure pump 151 is connected to the outlet 352 of the extraction chamber 350 via the collection chamber 325. As a result, the magnetic solution in the magnetic chamber 324 flows to the extraction chamber 350 via the chamber selection valve 330 under the negative pressure applied to the outlet 352 of the extraction chamber 350. Then, the magnetic solution passes through the porous membrane 120, and then is collected into the collection chamber 325.

Then, as shown in FIG. 6, a magnetic force from the outside of the collection chamber 325 may be applied to the magnetic solution to physically separate the magnetic solution from the elution solution, and then the elution solution may be recovered. Then, the target substance may be extracted from the elution solution.

FIG. 15 is a diagram to illustrate the experimental results using the fluidic chip according to the present disclosure. As described with reference to FIG. 15, it was tested whether the present scheme extracts a mutant gene at a very small proportion using a cfDNA standard sample. For comparative experiments, a commercially available centrifugation method, that is, QIA amp, was used. Moreover, Horizon product was used for the cfDNA standard sample used in the experiment. The sample volume is 500 μl. An experiment for extracting ctDNA of PIK3CA E545K, EGFR L858R, KRAS G12D, and NRAS Q61K from a total 4 samples set (0%, 0.1%, 1%, and 5%) was carried out. In FIG. 15, PIBEX refers to the experimental result of the fluidic chip according to the present disclosure.

As shown in FIG. 15, it may be identified that the amount of ctDNA extraction in the present scheme is almost the same as that in the QIA amp to which the conventional centrifugation method is applied. It may be identified that the ctDNA extraction is possible despite the very small percentage of mutations from 0.1% to 6%.

FIG. 16 is a diagram showing the experimental results of monitoring a mutant gene using blood analysis of a patient in actual clinical practice using a fluidic chip according to the present disclosure. PIK3CA H1047R mutation was monitored using 500 μl of plasma from HER-2 type breast cancer patients.

It may be identified that as cancer metastasis to the liver progresses, the mutant gene in the blood increases as shown in (b) in FIG. 16. Tumors that have metastasized to the liver may be identified using MRI images as shown in (a) in FIG. 16.

Although some embodiments of the present disclosure have been shown and described, it may be appreciated that those skilled in the art with ordinary skill in the art to which the present disclosure pertains may be able to modify those embodiments without departing from the principles or spirit of the present disclosure. The scope of the disclosure will be defined by the appended claims and their equivalents.

REFERENCE NUMERALS

100: extraction device 110: extraction kit
111: inlet 112: outlet
120: porous membrane 130: elution solution
140: magnetic solution 150: flow-driving force applicator
151: negative pressure pump 152: pressure gauge
300: fluidic chip 310: chip body
311: lower body 312: upper cover
321: sample chamber 322a, 322b, and 322c: washing chamber
323: elution chamber 324: magnetic chamber
325: collection chamber 326: waste solution chamber
330: chamber selection valve 331: gasket
332: chamber switching valve 333: first fixing jig
340: discharge selection valve 342: discharge switching valve
343: second fixing jig 350: extraction chamber
351: inlet 352: outlet
360: negative pressure inlet 371: flow channel

INDUSTRIAL APPLICABILITY

The method according to the present disclosure may extract a target substance such as a nucleic acid without using a centrifugation scheme or without applying high-speed centrifugation and thus may be usefully utilized in various industrial fields where the target substances such as nucleic acids are utilized.

What is claimed is:
1. A fluidic chip for extracting a target substance, the fluidic chip comprising:
   a chip body;
   a sample chamber formed inside the chip body that stores therein a sample solution containing the target substance;
   an elution chamber formed inside the chip body that stores therein an elution solution for elution of the target substance;
   a store chamber formed inside the chip body that stores therein a first solution having magnetism, wherein the first solution has a polarity different from a polarity of the elution solution such that the first solution is not mixed with the elution solution;
   an extraction chamber formed inside the chip body;
   a porous membrane installed inside the extraction chamber, wherein the target substance is bound to the porous membrane;
   a chamber selection valve installed on the chip body to selectively connect one of the sample chamber, the elution chamber, and the store chamber to the inlet of the extraction chamber; and a collection chamber formed inside the chip body and connected to the outlet of the extraction chamber;

wherein the chamber selection valve sequentially connects the extraction chamber to the elution chamber and the store chamber, and then a flow-driving force from an outside is applied such that the elution solution and the first solution respectively in the elution chamber and the store chamber sequentially pass through the inlet and then the porous membrane, wherein when the first solution passes through the porous membrane, the first solution expels the elution solution remaining in the porous membrane out of the membrane, and then the elution solution and first solution are collected into the collection chamber through the outlet.

2. The fluidic chip of claim 1, wherein the chip body comprises:

a lower body having the sample chamber, the elution chamber, the store chamber, the extraction chamber, and the collection chamber defined therein; and an upper cover coupled to a top face of the lower body, wherein flow channels for respectively connecting the sample chamber, the elution chamber, and the store chamber with the inlet of the extraction chamber are defined in the lower body, wherein a distal end of each of the flow channels and the inlet of the extraction chamber are open toward a top of the chip body, wherein the chamber selection valve is coupled to the lower body via the upper cover and selectively connects one of the distal ends of the flow channels respectively connected to the sample chamber, the elution chamber, and the store chamber to the inlet of the extraction chamber.

3. The fluidic chip of claim 2, wherein the fluidic chip further comprises:

at least one washing chamber defined in the lower body that stores therein a washing solution;

a waste solution chamber defined in the lower body that stores therein the sample solution and the washing solution that have passed through the extraction chamber; and a discharge selection valve coupled to the lower body via the upper cover to selectively connect the outlet of the extraction chamber to one of the collection chamber and the waste solution chamber, wherein after the target substance in the sample solution binds to the porous membrane, the washing solution in the washing chamber passes through the extraction chamber to wash the porous membrane.

4. The fluidic chip of claim 3, wherein the chip body further has a negative pressure inlet connected to the collection chamber and the waste solution chamber, wherein a negative pressure from an outside is introduced thereto through the negative pressure inlet, wherein the negative pressure inlet applies the negative pressure to the outlet of the collection chamber through the collection chamber or waste solution chamber based on selection of the discharge selection valve.

5. The fluidic chip of claim 1, wherein the elution solution is a polar solution, and the first solution is a non-polar solution.

6. The fluidic chip of claim 5, wherein when the target substance is a nucleic acid, the elution solution is polar distilled water or an elution buffer for nucleic acid extraction, and the first solution is non-polar mineral oil or silicone.

7. The fluidic chip of claim 1, wherein when the target substance is a nucleic acid, the porous membrane is selected from the group consisting of a silica membrane, an ion exchange resin, a silica mesh, a packing tube in which silica beads are packed, and a membrane having a surface having a functional group attached thereto capable of specific-binding to the target substance, or wherein when the target substance is selected from the group consisting of Circulating Tumor Cell (CTC), exosome, and a protein, the porous membrane is selected from a group consisting of an ion exchange resin and a membrane having a surface having a functional group attached thereto capable of specific-binding to the target substance.

8. The fluidic chip of claim 1, wherein the target substance is selected from the group consisting of DNA, RNA, CTC, exosome, and a protein.

* * * * *